United States Patent
Kubo et al.

(10) Patent No.: US 10,430,507 B2
(45) Date of Patent: Oct. 1, 2019

(54) REPORT CREATING SUPPORT APPARATUS, METHOD FOR THE SAME, AND COMPUTER-READABLE STORAGE MEDIUM

(71) Applicant: CANON KABUSHIKI KAISHA, Tokyo (JP)

(72) Inventors: Takeshi Kubo, Kyoto (JP); Yoshio Iizuka, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 182 days.

(21) Appl. No.: 14/320,798

(22) Filed: Jul. 1, 2014

(65) Prior Publication Data
US 2015/0026570 A1 Jan. 22, 2015

(30) Foreign Application Priority Data
Jul. 17, 2013 (JP) .................. 2013-148829

(51) Int. Cl.
*G06F 17/24* (2006.01)
*G16H 15/00* (2018.01)
*G06F 19/00* (2018.01)

(52) U.S. Cl.
CPC .......... *G06F 17/241* (2013.01); *G06F 17/243* (2013.01); *G06F 19/00* (2013.01); *G16H 15/00* (2018.01)

(58) Field of Classification Search
CPC .. G06F 19/322; G06F 17/243; G06F 19/3431; G06F 19/363; G06F 19/3487; G06F 3/048; G06F 17/241
See application file for complete search history.

(56) References Cited

U.S. PATENT DOCUMENTS

| | | | | |
|---|---|---|---|---|
| 4,763,356 A * | 8/1988 | Day, Jr. | ................. | G06F 3/0488 178/18.01 |
| 6,032,678 A * | 3/2000 | Rottem | ................. | G06F 19/324 128/920 |
| 8,684,807 B1* | 4/2014 | Crici | .................... | A63F 13/795 434/322 |

(Continued)

FOREIGN PATENT DOCUMENTS

| JP | 2004-355412 A | 12/2004 |
|---|---|---|
| JP | 2008-071365 A | 3/2008 |

(Continued)

OTHER PUBLICATIONS

Japanese office action issued in corresponding application No. 2013148829 dated Apr. 21, 2017.

(Continued)

*Primary Examiner* — Wilson W Tsui
(74) *Attorney, Agent, or Firm* — Carter, DeLuca & Farrell LLP

(57) ABSTRACT

A report creating support apparatus displays, on a display unit, an evaluation item associated with a diagnosis target and a plurality of evaluation values for the evaluation item, determines one indicated evaluation value from the plurality of evaluation values displayed, and superimposes criteria information of the indicated evaluation value and criteria information of not less than one evaluation value other than the indicated evaluation value among the plurality of evaluation values on display.

11 Claims, 4 Drawing Sheets

(56) References Cited

U.S. PATENT DOCUMENTS

| | | | | |
|---|---|---|---|---|
| 2001/0040587 | A1* | 11/2001 | Scheck | G01R 13/30 345/676 |
| 2004/0116779 | A1* | 6/2004 | Bien | A61B 5/16 600/300 |
| 2004/0268225 | A1* | 12/2004 | Walsh | G06F 17/30899 715/234 |
| 2005/0273363 | A1* | 12/2005 | Lipscher | G06Q 50/22 705/2 |
| 2007/0300145 | A1* | 12/2007 | Perelman | G06F 17/243 715/222 |
| 2008/0028289 | A1* | 1/2008 | Hicks | G06F 17/243 715/224 |
| 2008/0082909 | A1* | 4/2008 | Zuverink | G06F 3/0481 715/224 |
| 2010/0119131 | A1* | 5/2010 | Gebow | A61B 5/02007 382/128 |
| 2011/0064204 | A1* | 3/2011 | Clawson | H04M 11/04 379/45 |
| 2013/0132904 | A1* | 5/2013 | Primiani | G06F 3/048 715/834 |
| 2013/0179176 | A1* | 7/2013 | Gotthardt | G06F 19/345 705/2 |
| 2013/0268891 | A1* | 10/2013 | Finley | G06F 3/048 715/825 |
| 2014/0344753 | A1* | 11/2014 | Akasaka | G06F 3/0488 715/823 |

FOREIGN PATENT DOCUMENTS

| | | |
|---|---|---|
| JP | 2009-140228 A | 6/2009 |
| JP | 2009-238038 A | 10/2009 |
| JP | 2010-101660 A | 5/2010 |
| JP | 2012-133528 A | 7/2012 |

OTHER PUBLICATIONS

Japanese Office Action for application No. 2013-148829 dated Oct. 30, 2017 with English translation (7 pages).

* cited by examiner

FIG. 4A

[CONTOUR LINE]
ragged: ○ many / strong   ○ intermediate   ○ few / weak   ○ possible   ○ not recognized
spiculation: ○ many / strong   ○ intermediate   ○ few / weak   ○ possible   ○ not recognized
notch: ○ many / strong   ○ intermediate   ○ few / weak   ○ possible   ○ not recognized

FIG. 4B

[CONTOUR LINE]
ragged: ○ many / strong   ○ intermediate   ○ few / weak   ○ possible   ○ not recognized
spiculation: ○ many / strong   ○ intermediate   ○ few / weak   ○ possible   ○ not recognized
notch: ○ many / strong   ○ intermediate   ○ few / weak   ○ possible   ○ not recognized

FIG. 5

[CONTOUR LINE]
ragged: ○ many / strong   ○ intermediate   ○ few / weak   ○ possible   ○ not recognized
spiculation: ○ many / strong   ● intermediate   ○ few / weak   ○ possible   ○ not recognized
notch: ○ many / strong   ○ intermediate   ○ few / weak   ○ possible   ○ not recognized

REPORT CREATING SUPPORT APPARATUS, METHOD FOR THE SAME, AND COMPUTER-READABLE STORAGE MEDIUM

BACKGROUND OF THE INVENTION

Field of the Invention

The present invention relates to a report creating support apparatus, a method for the same, and a computer-readable storage medium.

Description of the Related Art

The results obtained when a doctor performs imaging diagnosis by observing medical images are compiled into an imaging diagnosis report. Recently, for the purpose of improving the efficiency of medical services, the computerization of medical documents has progressed, and imaging diagnosis reports have been electronically created. However, many conventional imaging diagnosis report creating support apparatuses are still designed to create a doctor input imaging findings and imaging diagnosis names in free text form. When writing reports in the free text form, different doctors use different terms and writing styles. In addition, reports sometimes contain writing errors. These make it difficult to implement automatic search and automatic analysis by using computers.

Under the circumstances, there has been proposed a report creating support apparatus based on a template form designed to make a doctor input information in the template form. The report creating support apparatus based on the template form enables the effective use of past imaging diagnosis reports by standardizing the written contents of the reports. Japanese Patent Laid-Open No. 2004-355412 discloses a report creating support apparatus which allows input operation in the free text form or template form. The apparatus disclosed in Japanese Patent Laid-Open No. 2004-355412 automatically creates finding sentences by making the user select graphics.

An imaging diagnosis report describes imaging findings associated with the abnormal shadow found by a doctor from a medical image and an imaging diagnosis name representing the determination of a medical classification name of the abnormal shadow. Imaging findings will be described in detail. The type of imaging finding (for example, a spiculation or notch) and its evaluation value (for example, "many" or "strong") are written in a report. In this case, both an imaging finding and imaging diagnosis name are often decided based on the knowledge and experience of a doctor. Therefore, doctors with different knowledge and experiences may add different evaluation values to each evaluation item (each imaging finding or imaging diagnosis name). In order to add evaluation values trusted by everyone, unified criteria can be provided for the respective evaluation items. The same applies to a case in which a report creating support apparatus based on the template form is used.

In order to make all doctors add evaluation values to each evaluation item according to unified criteria, it is possible to display information (an explanatory text or explanatory graphic to be referred to as criteria information hereinafter) indicating a criterion for each of a plurality of evaluation values for each evaluation item. If, however, pieces of criteria information concerning all evaluation values for all evaluation items existing in a template are collectively displayed, it takes a long time for a user (for example, a doctor; ditto for the following) to read all the information because of too much information. For this reason, the user may not read the criteria information when he/she is busy.

On the other hand, as a technique of displaying a small amount of information in a readably way, there is available a display technique called tooltip using a computer GUI (Graphic User Interface). Tooltip is a technique of displaying a small display frame on a given item only when the user points the cursor (mouse pointer) to the item, and displaying a small amount of information (a character string or icon) in the display frame. It is also possible to display a graphic in a display frame.

A plurality of evaluation values concerning each of many evaluation items (imaging findings and imaging diagnosis names) are displayed on an imaging diagnosis report in the template form. Using the above tooltip technique can display criteria information concerning an evaluation value for a given evaluation item. However, when adding an evaluation value to a given evaluation item, the user generally selects an optimal evaluation value upon comparing and studying a plurality of evaluation values. Therefore, there is a demand for simultaneously seeing criteria information concerning a plurality of evaluation values as comparison targets. However, when the above tooltip technique is used, only criteria information concerning one evaluation value to which the user points the cursor can be displayed. As a consequence, the user must move the cursor to a plurality of evaluation values as comparison targets one by one. Alternatively, the user needs to read a document collectively describing all pieces of criteria information concerning all evaluation values for all evaluation items.

SUMMARY OF THE INVENTION

The present invention provides a report creating support apparatus which can display, in a simple, readably way, the criteria information of a plurality of evaluation values of interest for a user so as to allow the user to add an evaluation value for each evaluation item according to unified criteria.

According to one aspect of the present invention, there is provided a report creating support apparatus comprising: a first display processing unit configured to display, on a display unit, an evaluation item associated with a diagnosis target and a plurality of evaluation values for the evaluation item; a determination unit configured to determine one indicated evaluation value from the plurality of evaluation values displayed by the first display processing unit; and a second display processing unit configured to superimpose criteria information of the indicated evaluation value and criteria information of not less than one evaluation value other than the indicated evaluation value among the plurality of evaluation values on display by the first display processing unit.

Further features of the present invention will become apparent from the following description of exemplary embodiments (with reference to the attached drawings).

BRIEF DESCRIPTION OF THE DRAWINGS

FIGS. 4A and 4B are views exemplifying the execution results of criteria information display processing (step S107); and FIG. 5 is a view exemplifying a report display window at the time of report inputting.

DESCRIPTION OF THE EMBODIMENTS

Figure 1:
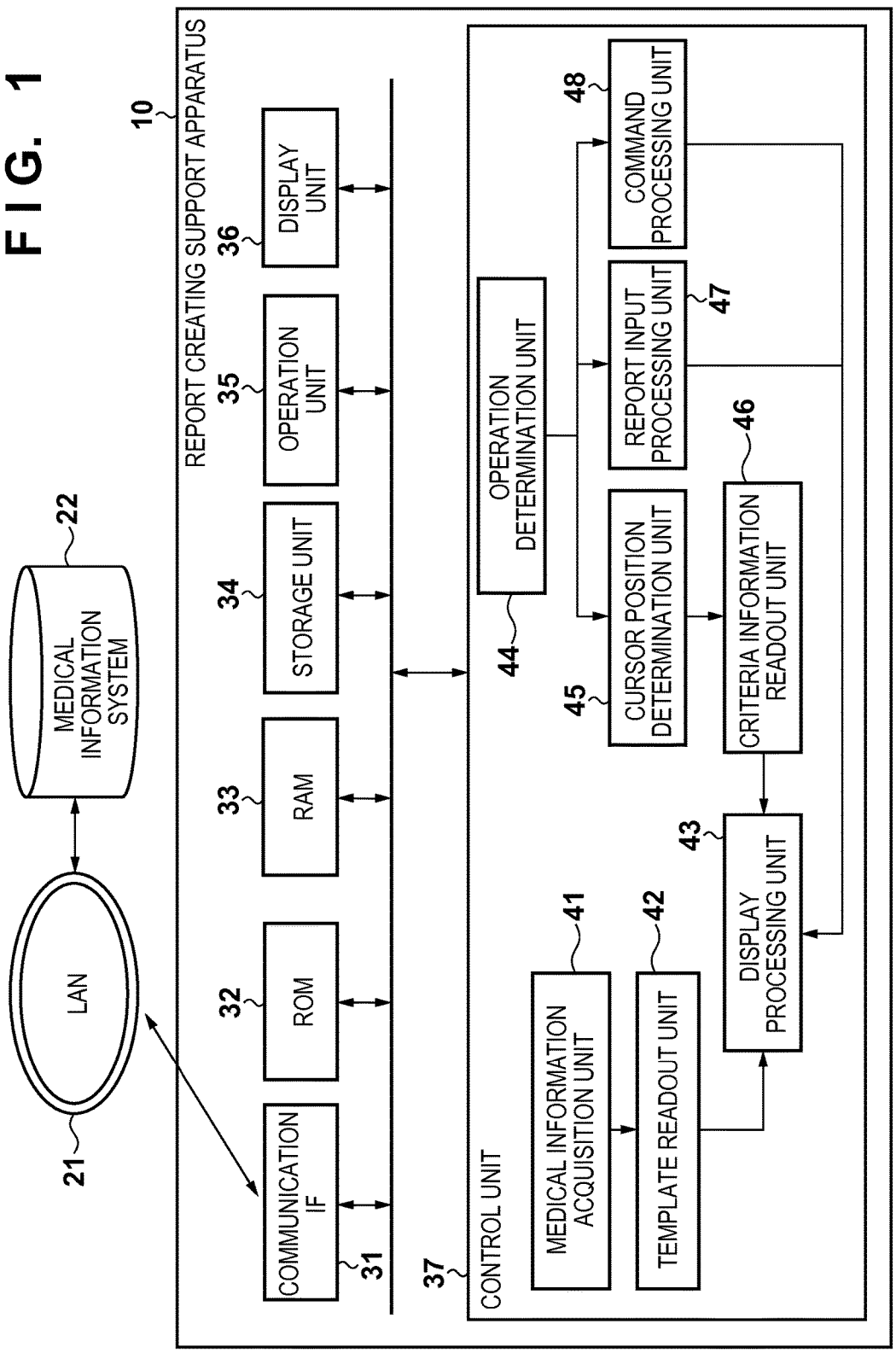
FIG. 1 is a block diagram showing an example of the overall arrangement of a report creating support apparatus according to the first embodiment.

The modes (embodiments) for carrying out the present invention will be described below with reference to the accompanying drawings. However, the scope of the present invention is not limited to the examples shown in the drawings.

First Embodiment

FIG. 1 is a block diagram showing an example of the overall arrangement of a report creating support apparatus according to the first embodiment. A report creating support apparatus 10 is communicatively connected to a medical information system 22 via a communication unit 21. In this embodiment, the communication unit 21 is formed from a LAN (Local Area Network). Although this embodiment will exemplify the case in which the communication unit 21 is formed from a LAN, the communication unit 21 is not limited to a LAN and may be formed from another type of network. The medical information system 22 manages various pieces of medical information such as patient information, doctor information, and past imaging diagnosis reports. The report creating support apparatus 10 saves the imaging diagnosis reports created by the processing described below in the medical information system 22 via the communication unit 21.

The report creating support apparatus 10 includes, as its functional components, a communication IF 31, a ROM 32, a RAM 33, a storage unit 34, an operation unit 35, a display unit 36, and a control unit 37. The communication IF (Interface) 31 is implemented by, for example, a LAN card, and controls communication between an external apparatus (for example, the medical information system 22 as a database) and the report creating support apparatus 10 via the communication unit 21. The ROM (Read Only Memory) 32 is implemented by a nonvolatile memory or the like, and stores various types of programs. The RAM (Random Access Memory) 33 is implemented by a volatile memory or the like, and temporarily stores various types of information. The storage unit 34 is implemented by, for example, an HDD (Hard Disk Drive), and stores various types of information such as a plurality of templates for imaging diagnosis reports which are created in advance for the respective pieces of attribute information of diagnosis target images. The operation unit 35 is implemented by a keyboard, a mouse, and the like, and inputs instructions from the user into the apparatus. The display unit 36 is implemented by a display or the like, and displays various types of information to the user.

The control unit 37 is implemented by, for example, a CPU (Central Processing Unit), and comprehensively controls processing in the report creating support apparatus 10. The control unit 37 is provided, as its functional components, a medical information acquisition unit 41, a template readout unit 42, a display processing unit 43, an operation determination unit 44, a cursor position determination unit 45, a criteria information readout unit 46, a report input processing unit 47, and a command processing unit 48. These components are implemented by making the CPU read and execute programs stored in the ROM 32, the storage unit 34, or the like using the RAM 33 as a work area.

Note that some or all of the components may be implemented by dedicated circuits and the like.

Figure 2:
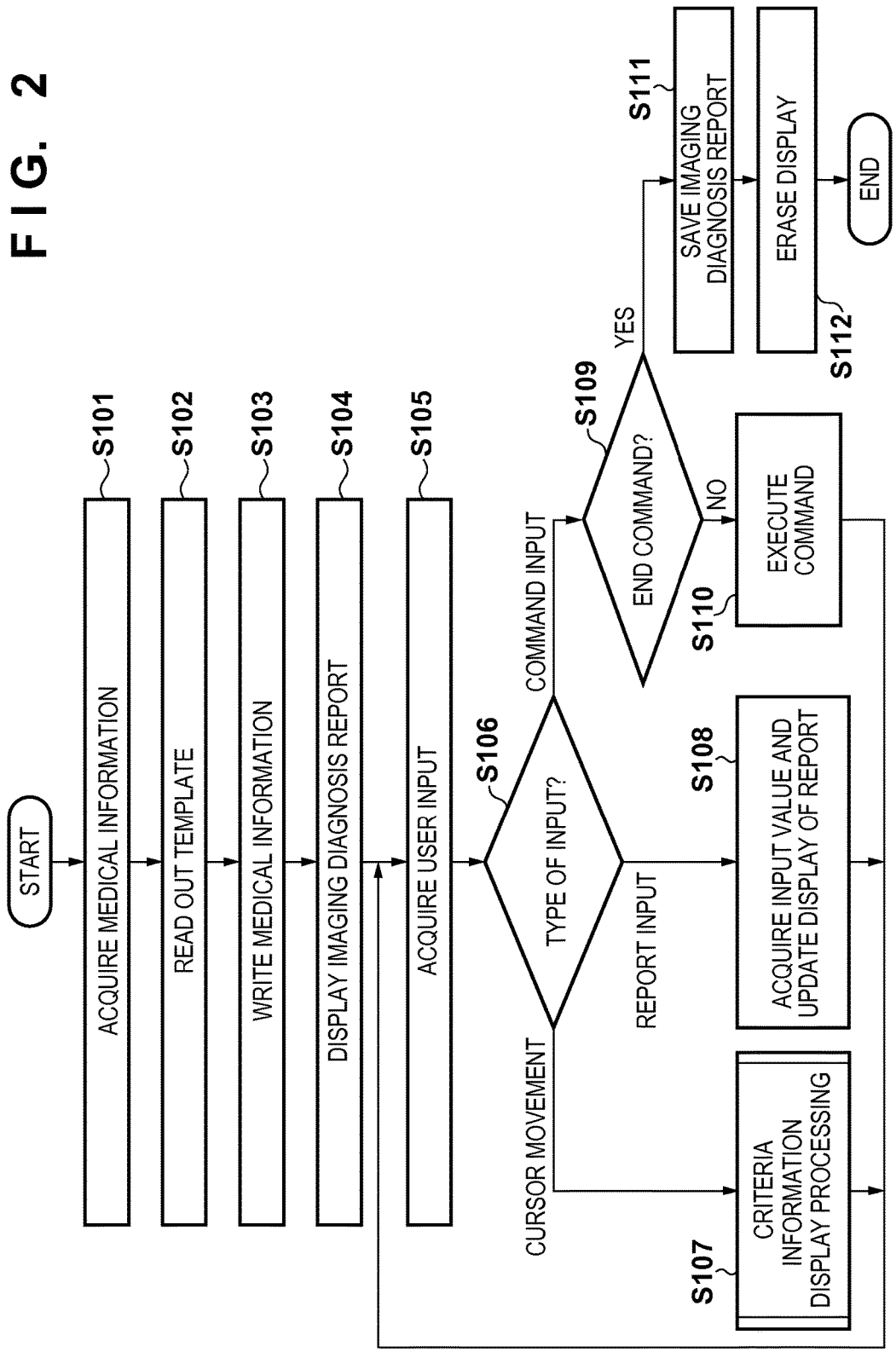
FIG. 2 is a flowchart showing an example of report creating support processing.

An example of processing in the report creating support apparatus 10 shown in FIG. 1 will be described next with reference to FIGS. 2 and 3. FIG. 2 is a flowchart showing report creating support processing in the report creating support apparatus 10. Referring to FIG. 2, when the user inputs a patient ID, an image ID, and a doctor ID as identification information via the operation unit 35 and indicates the start of creation of an imaging diagnosis report, the processing starts. When the processing starts, the medical information acquisition unit 41 uses the input patient ID, image ID, and doctor ID as search keys to acquire pieces of attribute information corresponding to the respective IDs as the attribute information of an image from the medical information system 22 via the communication unit 21 (step S101). For example, the user acquires the attribute information (the name, age, and the like) of the patient corresponding to the patient ID, the attribute information (the modality, imaging region, imaging date, and the like) of the image corresponding to the image ID, and the attribute information (the doctor name, the department to which the doctor belongs, and the like) of the doctor corresponding to the doctor ID. The medical information acquisition unit 41 stores the acquired attribute information of the image in the RAM 33.

The template readout unit 42 reads out an appropriate template for an imaging diagnosis report from the storage unit 34 in accordance with the attribute information of the image acquired by the medical information acquisition unit 41, and stores the imaging diagnosis report in an initial state in the RAM 33 (step S102). If, for example, the attribute information of the image is [modality: CT, imaging region: chest], the template readout unit 42 reads out a template for chest CT and stores it in the RAM 33. The template for an imaging diagnosis report contains an attribute information field for the patient, an attribute information field for the doctor who performs imaging diagnosis, predetermined evaluation items (imaging findings and imaging diagnosis name), and options for evaluation values for the respective items. As will be described later, the user creates an imaging diagnosis report by selecting an evaluation value for each evaluation item. The template readout unit 42 writes the patient attribute information and the doctor attribute information acquired by the medical information acquisition unit 41 in the corresponding fields of the imaging diagnosis report stored in the RAM 33 (step S103).

The display processing unit 43 displays the imaging diagnosis report, which the template readout unit 42 writes in the RAM 33, on the display unit 36 in the first display processing (step S104). The user creates an imaging diagnosis report while seeing the image as a diagnosis target displayed on a medical image display apparatus (not shown). After the imaging diagnosis report is displayed in step S104, the operation determination unit 44 acquires the user input which is input from the operation unit 35 (step S105). The operation determination unit 44 then transfers the input information to any one of the cursor position determination unit 45, the report input processing unit 47, and the command processing unit 48 in accordance with the type of input (step S106). More specifically, if the input content is cursor movement, the operation determination unit 44 transfers the cursor movement information to the cursor position determination unit 45. If the input content is a report, the operation determination unit 44 transfers the report input information to the report input processing unit 47. If the input content is a command, the operation determination unit 44 transfers the command input information to the command processing unit 48. The cursor position determination unit 45, the report input processing unit 47, and the command processing unit 48 then perform operations in accordance with the respective pieces of input information (steps S107 to S109).

The cursor position determination unit 45 acquires the cursor movement information from the operation determination unit 44, and performs processing in accordance with the acquired information (step S107). More specifically, the cursor position determination unit 45 performs criteria information display processing together with the criteria information readout unit 46 and the display processing unit 43. The criteria information display processing is the processing of simultaneously displaying the criteria information of the evaluation value indicated by the cursor position and the criteria information of neighboring evaluation values. This processing will be described later with reference to FIG. 3.

The report input processing unit 47 acquires the report input information from the operation determination unit 44, and performs processing in accordance with the acquired information (step S108). Assume that report input information in this embodiment is, for example, information (selection information) which indicates the selection of an evaluation value for a predetermined evaluation item. At this time, when one evaluation value is selected concerning one evaluation item, the report input processing unit 47 cancels the selection of all the remaining values included in the evaluation item. This prevents two or more evaluation values from being simultaneously selected concerning one evaluation item. In addition, upon writing the selected states of all evaluation values concerning all evaluation items in the imaging diagnosis report stored in the RAM 33, the report input processing unit 47 notifies the display processing unit 43 of the update of the display (step S108). Upon receiving the notification from the report input processing unit 47, the display processing unit 43 reads out the imaging diagnosis report stored in the RAM 33 and displays the report on the display unit 36. FIG. 5 shows a display example on the display unit 36. FIG. 5 is a view exemplifying the report display window at the time of report inputting. Referring to FIG. 5, the evaluation value "intermediate" is selected concerning "spiculation" as an evaluation item.

The command processing unit 48 acquires command input information from the operation determination unit 44, and performs processing in accordance with the acquired information (step S108). If the command input information indicates a command other than an end command (NO in step S109), the command processing unit 48 processes the corresponding command (step S110). If the command input information indicates an end command (YES in step S109), the command processing unit 48 saves the imaging diagnosis report stored in the RAM 33 in the medical information system 22 via the communication IF 31 and the communication unit 21 (step S111). The command processing unit 48 then notifies the display processing unit 43 of the end of report creation. The display processing unit 43 updates the window displayed on the display unit 36 in accordance with the notification received from the command processing unit 48. Upon receiving the report creation end notification, the display processing unit 43 erases the display of the imaging diagnosis report (step S112). With the above operation, the imaging diagnosis report creating support processing is terminated. Note that after the execution of steps S107, S108, and S110, the process returns to step S105 again.

Figure 3:
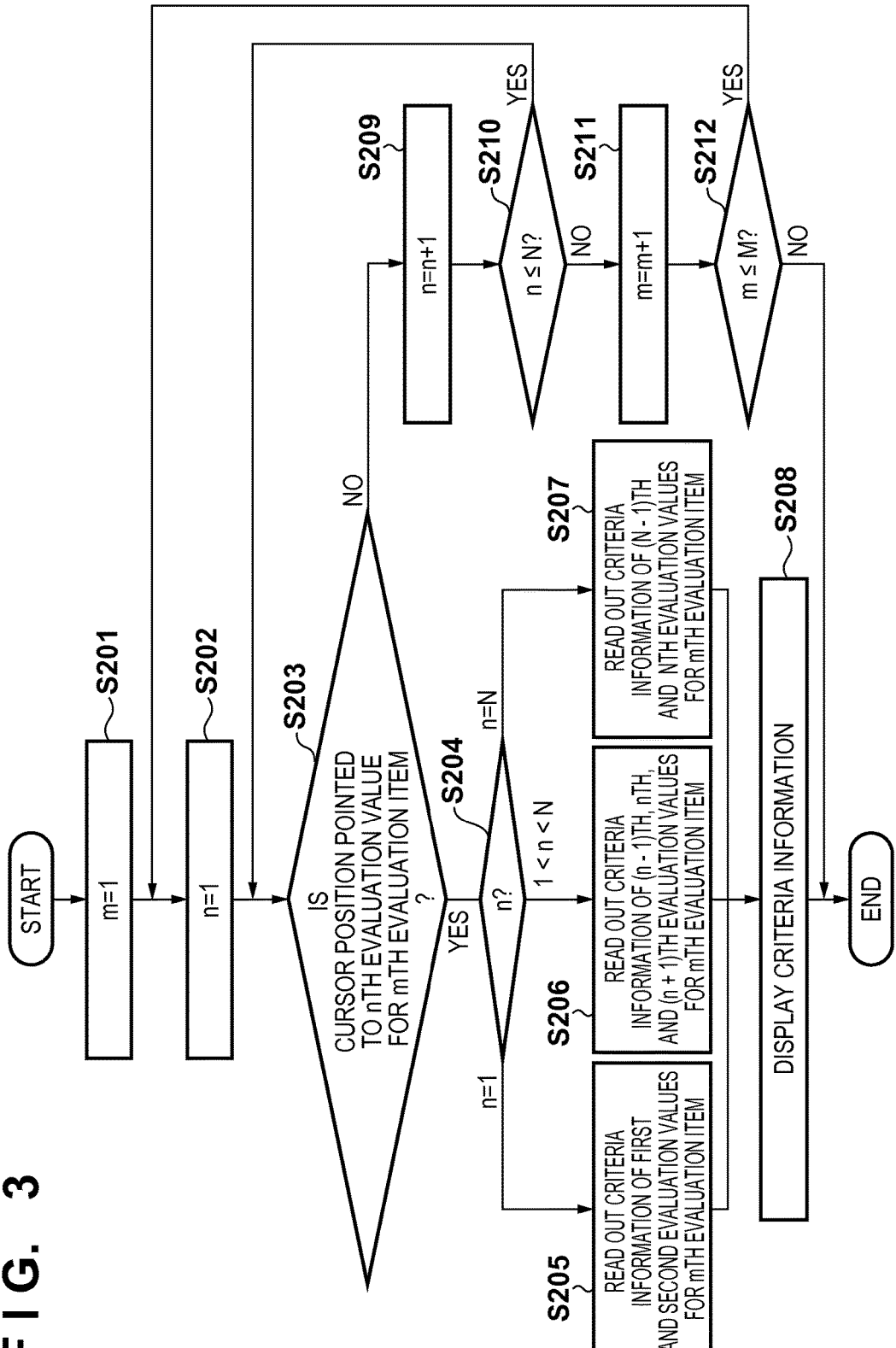
FIG. 3 is a flowchart showing an example of criteria information display processing (step S107)

FIG. 3 is a flowchart showing an example of criteria information display processing (step S107). Referring to FIG. 3, when the cursor position determination unit 45 receives cursor position information from the operation determination unit 44, processing starts. When the processing starts, the cursor position determination unit 45 substitutes 1 into an identifier m of the evaluation item first (step S201), and substitutes 1 into an identifier n of an evaluation value for the mth evaluation item (step S202). The cursor position determination unit 45 then determines whether the cursor position received from the operation determination unit 44 matches the position of the nth evaluation value for the mth evaluation item (step S203). If the positions match each other, the process advances to step S204. If the positions do not match each other, the process advances to step S209.

In step S209, the cursor position determination unit 45 adds 1 to the value n (step S209), and determines whether the value n is equal to or less than a total number N of evaluation values for the mth evaluation item (step S210). If the value n is equal to or less than N, the process returns to step S203. If the value n exceeds N, the process advances to step S211. In step S211, the cursor position determination unit 45 adds 1 to the value m (step S211), and determines whether the value m is equal to or less than the total number M of evaluation items (step S212). If the value m is equal to or less than M, the process returns to step S202. If the value m exceeds M, the processing is terminated.

In step S204, the criteria information readout unit 46 determines whether the value n is 1, equal to or more than 2 and less than N, or N, and decides criteria information to be read out in accordance with the determination result (step S204). If the value n is 1, the criteria information readout unit 46 reads out the criteria information of the first and second evaluation values for the mth evaluation item (step S205). If the value n is equal to or more than 2 and less than N, the criteria information readout unit 46 reads out the criteria information of the (n−1)th, nth, and (n+1)th evaluation values for the mth evaluation item (step S206). If the value n is N, the criteria information readout unit 46 reads out the criteria information of the (N−1)th and N evaluation values for the mth evaluation item (step S207). That is, the criteria information readout unit 46 reads out the criteria information of evaluation values adjacent to the nth evaluation value, which are evaluation values other than the nth evaluation value. The criteria information readout unit 46 transfers the readout criteria information to the display processing unit 43.

The display processing unit 43 collectively displays, at a predetermined position on the display unit 36, a plurality of pieces of criteria information transferred from the criteria information readout unit 46 in the second display processing (step S208). In this case, the first example of a predetermined position is a relatively small display frame which is temporarily displayed at the cursor position. This embodiment differs from the conventional tooltip technique in that the pieces of criteria information of a plurality of evaluation values at the cursor position and its neighboring positions are collectively displayed. In addition, the second example of the predetermined position is a predetermined display frame determined in advance on the display unit 36. For example, one of the positions of the four corners of the window displayed on the display unit 36 is determined as a predetermined display frame display position in advance. This predetermined display frame may be temporarily displayed only when a plurality of pieces of criteria information are transferred from the criteria information readout unit 46 or may be constantly displayed. When such information is to be constantly displayed, the plurality of pieces of criteria information finally transferred from the criteria information readout unit 46 are displayed.

With processing in steps S205 to S207 and processing in step S208, the criteria information of the evaluation value to which the cursor position is pointed and the criteria information of evaluation values adjacent to the evaluation value are simultaneously displayed. In the processing of displaying the above pieces of criteria information, the display method for a display frame may be changed in accordance with a predetermined user instruction, or the processing may be switched to the processing of displaying nothing in accordance with a predetermined user instruction.

FIGS. 4A and 4B are views exemplifying the execution results of the criteria information display processing (step S107) described with reference to FIG. 3. In the examples shown in FIGS. 4A and 4B, "ragged", "spiculation", and "notch" are displayed as evaluation items, the characters "many/strong", "intermediate", "few/weak", "possible", and "not recognized" are displayed as evaluation candidates for the respective items, together with radio buttons each for indicating one of the candidates. The control unit 37 sets an evaluation concerning an evaluation item on an image in accordance with the input operation of moving the cursor displayed on the display unit 36 in accordance with an operation input to the operation unit 35 and clicking a radio button corresponding to one of the candidates. For example, while a medical image of an evaluation target is indicated, the control unit 37 sets the evaluation value "intermediate" for the evaluation item "ragged" concerning the medical image of the evaluation target in accordance with the input operation of selecting the evaluation value "intermediate" concerning the evaluation item "ragged" in FIGS. 4A and 4B. In addition, in accordance with the input operation of selecting the evaluation value "few/weak" for the evaluation item "spiculation", and the evaluation value "not recognized" for the evaluation item "notch", the control unit 37 sets the evaluation values.

FIG. 4A shows a display example when the cursor position is pointed to none of the evaluation values concerning all the evaluation items ("ragged", "spiculation", and "notch"). That is, this is a display example when it is determined in step S212 in FIG. 3 that the value m has exceeded M. In this case, the processing in step S107 is terminated, and the process returns to step S105 in FIG. 2.

FIG. 4B shows a display example when the cursor position is pointed to one evaluation value concerning one evaluation item. More specifically, FIG. 4B shows a display example when the cursor position is pointed to the evaluation value "intermediate" concerning the evaluation item "spiculation". That is, FIG. 4B shows a display example when it is determined in step S204 in FIG. 3 that the value n is equal to or more than 2 and less than N. In the example shown FIG. 4B, evaluation item names, evaluation value names, and explanatory graphics (illustrations) of evaluation values are displayed as criteria information superimposed (popup-displayed) on the foreground screen. Referring to FIG. 4B, the explanatory graphics displayed in the form of illustrations include an explanatory graphic of the evaluation value "intermediate" and explanatory graphics of evaluation values ("many/strong" and ""few/weak") adjacent to the evaluation value "intermediate". Note that although FIG. 4B shows the explanatory graphics of the evaluation values in the form of illustrations, the present invention is not limited to this, and real medical images may be displayed. In addition, a plurality of graphics (illustrations or medical images) may be displayed for one evaluation value instead of one explanatory graphic (illustration or medical image) for one evaluation value. Such explanatory information can be created in a predetermined form in advance by a vendor or user and stored in the storage unit 34.

As described above, according to the present invention, it is possible to simultaneously display a plurality of pieces of criteria information of an evaluation value of interest and its neighboring evaluation values in a readable way by the simple operation of making the user point the cursor to an evaluation value of the evaluation item of interest. That is, the user can compare the criteria information of the evaluation value of interest with the criteria information of neighboring evaluation values, and hence can efficiently understand the criteria information of each evaluation value. This makes it possible to create imaging diagnosis reports according to unified criteria.

Although this embodiment has exemplified the patient ID, the image ID, and the doctor ID as information required to start creating an imaging diagnosis report, the present invention is not limited to them, and other types of information may be used. Likewise, in the embodiment, the template readout unit 42 reads out a template corresponding to the attribute information of an image as an imaging diagnosis report in an initial state from the storage unit 34. However, the template readout unit 42 may read out a template based on other types of identification information. In addition, the embodiment is configured to simultaneously display the criteria information of the evaluation value to which the cursor position is pointed and the criteria information of evaluation values adjacent to the evaluation value. However, all the pieces of criteria information in the same evaluation item may be displayed. Furthermore, this display operation is not limited to simultaneous display, and display operation may be performed in any form that can be visually recognized by the user. For example, pieces of criteria information may be switched and displayed at predetermined time intervals.

As has been described above, according to this embodiment, when the criteria information of the evaluation value indicated by the cursor is displayed (popup-displayed) on the foreground screen, the pieces of criteria information of other evaluation values are additionally presented. This allows the user to easily select an evaluation value. Note that "evaluation value" is not limited to a numerical value and may include an evaluation corresponding to an evaluation item, such as "many/strong", "intermediate", "few/weak", "possible", or "not recognized", as shown in FIGS. 4A and 4B. Alternatively, "evaluation value" may include an evaluation that cannot be converted to a numerical value, such as "sphere", "lobular", "wedged", or "ragged", when an evaluation item is "shape".

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-148829, filed Jul. 17, 2013 which is hereby incorporated by reference herein in its entirety.

What is claimed is:

1. An imaging diagnosis report creating support apparatus comprising:
one or more processors; and
one or more memories coupled to the one or more processors and having instructions stored thereon which, when executed by the one or more processors, cause the report creating support apparatus to:
cause a display unit to display a plurality of evaluation values for an evaluation item associated with an imaging diagnosis target, wherein the plurality of evaluation values are arranged in order in accordance with a state of the imaging diagnosis target, and the evaluation item is an item related to an imaging finding;
in a case where a mouse cursor is moved to a position at one of the displayed evaluation values, determine a number of the evaluation values to display adjacent to an indicated evaluation value at the position of the mouse cursor;
while the mouse cursor is at the position of the indicated evaluation value, obtain a subset of evaluation values from the displayed evaluation values adjacent to the indicated evaluation value based on the determined number, and cause the display unit to display in a popup, based on the obtaining, the subset of evaluation values and the indicated evaluation value, and wherein a graphic illustrates a criterion for the indicated evaluation value in the popup and a graphic illustrates a criterion for the displayed subset of evaluation values adjacent to the indicated evaluation value in the popup, in such a manner that the popup is displayed at the position of the mouse cursor; and
in a case where one of the subset of evaluation values or indicated evaluation value is selected in the popup or display by clicking, store, as an imaging diagnosis report for the imaging diagnosis target, the selected evaluation value for the item in the one or more memories.

2. The apparatus according to claim 1, wherein the popup is a predetermined display frame.

3. The apparatus according to claim 1, wherein the instructions, when executed by the one or more processors, further cause the apparatus to cause the display unit to switch and display the graphic illustrating the criterion for the indicated evaluation value and the at least one graphic illustrating the criterion for the evaluation value adjacent to the indicated evaluation value at predetermined time intervals.

4. The apparatus according to claim 1, wherein the evaluation item and the plurality of evaluation values are selected based on identification information input by a user.

5. The apparatus according to claim 4, wherein the identification information is attribute information of an image as the imaging diagnosis target.

6. The apparatus according to claim 1, wherein the graphic is an illustration or a medical image.

7. The apparatus according to claim 1, wherein the instructions, when executed by the one or more processors, further cause the apparatus to cause the display unit to hide the graphic illustrating the criterion for the indicated evaluation value and the graphic illustrating the criterion for the evaluation value adjacent to the indicated evaluation value, in a case where the one of the evaluation values is selected by clicking.

8. The apparatus according to claim 1, wherein the instructions, when executed by the one or more processors, further cause the apparatus to cause the display unit to display nothing by a predetermined user instruction.

9. An imaging diagnosis report creating support method comprising:
causing a display unit to display a plurality of evaluation values for evaluation item associated with an imaging diagnosis target, wherein the plurality of evaluation values are arranged in order in accordance with a state of the imaging diagnosis target, and the evaluation item is an item related to an imaging finding;
in a case where a mouse cursor is moved to a position at one of the displayed evaluation values, determining a number of the evaluation values to display adjacent to an indicated evaluation value at the position of the mouse cursor;
while the mouse cursor is at the position of the indicated evaluation value, obtaining a subset of evaluation values from the displayed evaluation values adjacent to the indicated evaluation value based on the determined number, and causing the display unit to display in a popup, based on the obtaining, the subset of evaluation values and the indicated evaluation value, and wherein a graphic illustrates a criterion for the indicated evaluation value in the popup and a graphic illustrates a criterion for the displayed subset of evaluation values adjacent to the indicated evaluation value in the popup, in such a manner that the popup is displayed at the position of the mouse cursor; and
in a case where one of the subset of evaluation values or indicated evaluation value is selected in the popup or display by clicking, storing, as an imaging diagnosis report for the imaging diagnosis target, the selected evaluation value for the item in one or more memories.

10. A non-transitory computer-readable storage medium storing a computer program for controlling a computer to execute an imaging diagnosis report creating support method, the method comprising:
causing a display unit to display a plurality of evaluation values for evaluation item associated with an imaging diagnosis target, wherein the plurality of evaluation values are arranged in order in accordance with a state of the imaging diagnosis target, and the evaluation item is an item related to an imaging finding;
in a case where a mouse cursor is moved to a position at one of the displayed evaluation values, determining a number of the evaluation values to display adjacent to an indicated evaluation value at the position of the mouse cursor;

while the mouse cursor is at the position of the indicated evaluation value, obtaining a subset of evaluation values from the displayed evaluation values adjacent to the indicated evaluation value based on the determined number, and causing the display unit to display in a popup, based on the obtaining, the subset of evaluation values and the indicated evaluation value, and wherein a graphic illustrates a criterion for the indicated evaluation value in the popup and a graphic illustrates a criterion for the displayed subset of evaluation values adjacent to the indicated evaluation value in the popup, in such a manner that the popup is displayed at the position of the mouse cursor; and in a case where one of the subset of evaluation values or indicated evaluation value is selected in the popup or display by clicking, storing, as an imaging diagnosis report for the imaging diagnosis target, the selected evaluation value for the item in one or more memories.

11. The apparatus according to claim 1, wherein the instructions, when executed by the one or more processors, further cause the apparatus to cause the display unit to display the graphic illustrating the criterion for the indicated evaluation value and at least one graphic illustrating the criterion for any evaluation value adjacent to the indicated evaluation value and to display text describing the indicated evaluation value and at least one text describing any evaluation value adjacent to the indicated evaluation value which is a part of the plurality of evaluation values.

* * * * *